L. ELL

Aug. 8, 1933. VACUUM CLEANER Re. 18,915

Original Filed Feb. 28, 1930

INVENTOR
Lars Ell
BY
Wm. J. Hedlund
his ATTORNEY

Reissued Aug. 8, 1933

Re. 18,915

UNITED STATES PATENT OFFICE 18,915

VACUUM CLEANER

Lars Ell, Stockholm, Sweden, assignor, by mesne assignments, to Electrolux Corporation, a Corporation of Delaware Original No. 1,842,900, dated January 26, 1932, Serial No. 432,185, application February 28, 1930, and in Germany May 16, 1929. Application for reissue November 3, 1932. Serial No. 641,070

13 Claims. (Cl. 167—3)

This invention relates to vacuum cleaners and like devices employing a current of air and operating to clean materials and/or treat air. More particularly the invention relates to vacuum cleaners and like apparatus employing an air conditioning substance such as a disinfectant or insecticide and still more particularly to such apparatus comprising, in combination with other parts thereof, a receptacle for vaporizable material and to mechanism for detachably mounting this receptacle in the air stream of the cleaner. The invention provides for using a vacuum cleaner for disinfecting insecticidal and perfuming purposes by incorporating a vapor having suitable characteristics in the air stream produced by the cleaner, the receptacle being so constructed and so positioned that vapors are efficiently adsorbed by the air stream. The receptacle, which in itself constitutes one phase of the invention, is constructed so that it may be mounted in the cleaner unit with a minimum alteration thereof and may be readily removed and stored while the cleaner is operated for usual cleaning purposes.

One object of the invention is to provide means for efficiently applying vapors to the air current of the vacuum cleaner.

Other objects of the invention are: to provide a detachable receptacle for vaporizable material which is adapted to be applied to a vacuum cleaner in a convenient and simple manner; to incorporate means in the receptacle to cause the air current therein to agitate and thoroughly permeate the contents thereof; to provide means for heating the air before it is applied to the receptacle; to provide a material having a low surface tension whereby the vapors therefrom may be readily adsorbed in an air stream; to provide a container for said material in which the material may be transported and which is suitable for attachment to a vacuum cleaner whereby the necessity for handling the material is eliminated; to provide a container which may be sealed during shipment to prevent excessive vaporization of the material contained therein, the seal to be readily removable before the container is attached to the vacuum cleaner; to provide a device of the above character which may be applied to either the suction or blower ports of a vacuum cleaner; and to provide a relatively simple, dependable, highly efficient and convenient device for the purpose above indicated.

The invention also consists in certain other new and original features of construction and combinations of parts hereinafter set forth and claimed.

Figure 1:
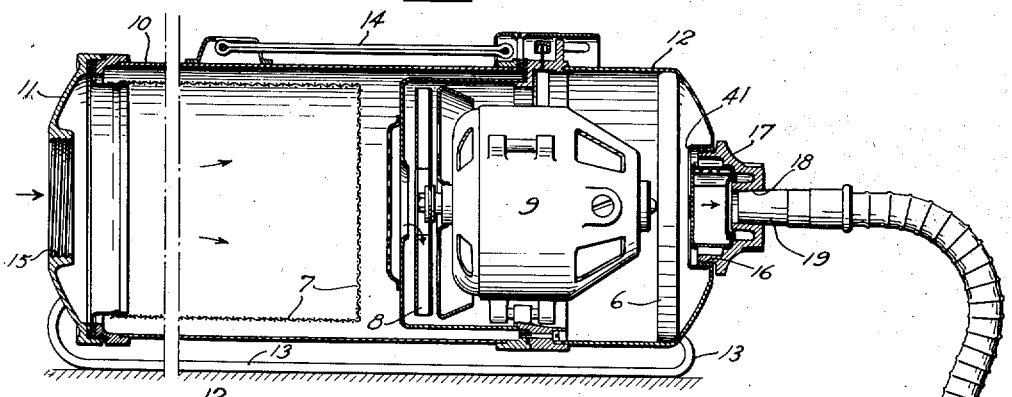
Figure 2:
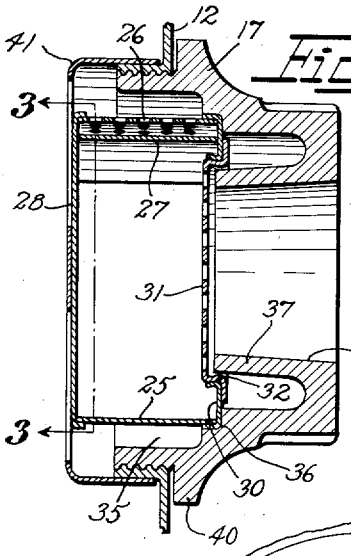
Figure 3:
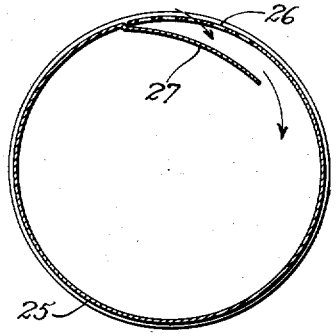
Figure 3:
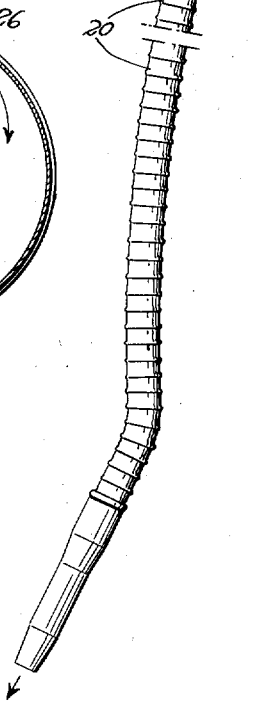
Figure 4:
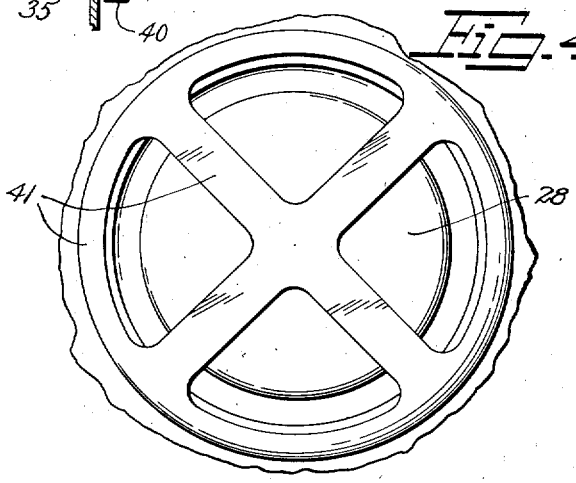

Although the novel features which are believed to be characteristic of this invention will be particularly pointed out in the claims appended hereto, the invention itself, as to its objects and advantages the mode of its operation and the manner of its organization may be better understood by referring to the following description taken in connection with the accompanying drawing forming a part thereof in which Fig. 1 is an assembly view principally in cross-section of a vacuum cleaner constructed in accordance with the present invention; Fig. 2 is a longitudinal sectional view of the coupling and receptacle; Fig. 3 is a transverse sectional view of the receptacle taken on the line 3—3 of Fig. 2; and Fig. 4 is an end view of the container showing a portion of the cleaner associated therewith.

Like reference characters denote like parts in the several figures of the drawing.

In the following description and in the claims parts will be identified by specific names for convenience but they are intended to be as generic in their application to similar parts as the state of the art will permit.

Referring to the drawing more in detail, there is shown a vacuum cleaner unit having a casing comprising a barrel 10, to the ends of which are secured bell 11 and housing 12. Housing 12 contains a blower 8 and driving motor 9 by which the cleaner is operated to produce a current of air in the direction of the arrows. Runners 13, which are secured to the ends of barrel 10, provides means for supporting the cleaner on a surface. Handle 14 is suitably connected to the cleaner to permit the same to be readily handled. A dust bag 7 is removably contained in the barrel 10, clamps being provided for releasing bell 11 to remove the dust bag. There is also a filter 6 through which all the air must pass, this filter serving to separate out certain impurities.

Bell 11 and housing 12 are formed with similar central openings or ports 15 and 16, respectively, which are internally threaded to receive a coupling 17. Coupling 17 is formed with an internal bore 18 which is adapted to receive the tapered end 19 of a flexible air hose 20 of conventional construction. By screwing coupling 17 into bell 11 and inserting the air hose therein, the device may be used to suck air, as in cleaning carpets. In this case, the bore 18 of the coupling is the inlet port of the cleaner unit while opening 16 is the outlet port. By screwing coupling 17 into housing 12 and inserting the air hose therein, the device may be used as a blower. In this case, the opening 15 is the inlet port of the cleaner unit while bore 18 of the coupling is the outlet port.

Referring to Figs. 2, 3 and 4, the receptacle is shown as comprising a wall 25 formed from a strip of flexible material such as tin plate, cardboard or similar material one end of which is provided with perforations 26. The other end is bent to overlap these perforations and forms a guiding vane 27 for the purpose to be described. Bottom 28 may be secured to side wall 25 in any conventional manner. Attached to said side wall and extending inwardly therefrom at the top of said receptacle is an annular flange 30 in which a perforated cover 31 is seated and secured by frictional engagement. The edge of cover 31 may be formed with a slight groove 32 to facilitate attachment thereof to flange 30 and to form a more rigid assembly. It is to be noted that the cover may be removed by springing the part adjacent groove 32 past flange 30 and may be applied merely by the application of pressure.

The receptacle is positioned during use in a compartment formed between coupling 17 and the stationary portion of the vacuum cleaner. For this purpose a spider 41 is attached adjacent opening 16 of housing 12. This spider is of concave form and is adapted to receive the receptacle with the bottom 28 contacting the spider and to position the same with respect to housing 12. Coupling 17 is formed with a suitable recess 35 to receive the receptacle and is provided with an annular groove 36 against which the receptacle is securely seated when the parts are in assembled position. Annular flange 37 extends to a point adjacent cover 31 of the receptacle and directs air currents therefrom into the tapered end 19 of the air hose. Shoulder 40 contacts with housing 12 to form a seal when the coupling is used without the receptacle in normal cleaning operations.

In using the above described device for incorporating a vapor in the air stream of the cleaner, it is preferable to employ a material having a low surface tension so that the material is readily vaporized when an air current is passed over the surface thereof. The particular material employed will depend upon the purpose for which the device is to be used. For insecticidal purposes para-dichlorobenzol and para-dibromobenzol crystals may be employed. Bornyl acetate is an example of a readily vaporizable perfume. While it is preferable to use finely divided solid materials such as the crystals above mentioned, it is obvious that other types of disinfectants, germicides or perfumes may be employed, such as gaseous or liquid materials, adsorbed in a solid, for example, infusorial earth.

The receptacle is normally filled with the desired material and may be sealed, as by oiled paper or other similar means, to prevent evaporation of the contents thereof. Vane 27 may be positioned in contact with the wall 25 of the receptacle to form a closure for perforations 26. In this case vane 27 must be bent inwardly to the position shown in Fig. 3 before the device is operated.

To assemble the elements the seal is removed from the receptacle which is inserted in opening 16 of housing 12 and positioned against spider 41. Coupling 17 is then placed in position and the receptacle is clamped between annular recess 36 of the coupling and spider 41 so that all movement of the receptacle is prevented. The coupling is designed so that a slight clearance is obtained between shoulder 40 thereof and the housing 12 when the receptacle is in position, whereby the receptacle may be securely gripped between the elements above mentioned.

When the cleaner is operated the air stream therein passes through the dust bag and over the driving motor and then passes through perforations 26 into the receptacle, from which it is discharged through the perforations in cover 31. The air entering the receptacle is caused to rapidly whirl, due to the action of vane 27. Sufficient rotary motion may be obtained to agitate the particles of material in the receptacle and to effect a thorough contact with all parts of the surface thereof. The motion of the air and particles in the receptacle is parallel to the surface of cover 31. Hence the tendency of the particles to become lodged in the perforations is reduced to a minimum. The air becomes heated in passing over the motor and is applied to the receptacle in a heated condition, thereby imparting heat to the surface of the material within the receptacle and accelerating the vaporization thereof. The vapor is picked up and absorbed by the air current and is carried therewith through air hose 20 and discharged therefrom. This vapor laden air may be used for the various purposes above mentioned, depending upon the particular material employed in the receptacle, and may be conveniently directed by the air hose upon the desired objects.

Annular recess 36, which seats against the receptacle, prevents passage of air around the sides of said receptacle and causes all of the air from the device to pass through the receptacle before being applied to the air hose.

While certain novel features of the invention have been shown and described and are pointed out in the annexed claims, it will be understood that various omissions, substitutions and changes in the forms and details of the device illustrated and in its opertion may be made by those skilled in the art without departing from the spirit of the invention.

What I claim is:

1. A receptacle for vaporizable material having a substantially cylindrical outside wall, an air inlet in said cylindrical wall, a peripheral vane adjacent said air inlet, and an axial air outlet, said vane causing the air to whirl in said receptacle and to agitate the material therein.

2. A receptacle adapted for flow of air therethrough comprising a substantially cylindrical element having peripheral air inlet perforations, and a guiding vane mounted adjacent said perforations for directing flow of air within said receptacle, said receptacle having an axial air outlet.

3. A receptacle of substantially cylindrical form having peripheral air inlet perforations, and a guiding vane mounted therein adjacent said perforations and in a position to cause the air to whirl within said receptacle, one end of said receptacle being perforated to permit escape of air therefrom.

4. A receptacle comprising a substantially cylindrical wall formed from a flexible material, said wall being extended inwardly of said receptacle to form a guiding vane, the portion of said wall adjacent said vane having perforations for the admission of air, said vane serving to direct the air interiorly thereof and cause the same to agitate the contents of said receptacle.

5. In a vacuum cleaner, a stationary casing member having an opening for discharge of air, a coupling member fitting said opening for connecting an air hose to said casing member, and a receptacle for vaporizable materal, said casing member and said coupling member forming a compartment for receiving said receptacle.

6. In a vacuum cleaner, a stationary casing member having an opening for discharge of air, a coupling member fitting said opening for connecting an air hose to said casing member, said coupling member having a recess, a container adapted to seat in said recess, and means for holding said container in said casing member clamped against said coupling member.

7. In a vacuum cleaner, a casing member having an opening for discharge of air, a coupling member adapted to seat in said opening, a circular container adapted to be inserted in said opening, and means for holding said container clamped between said coupling member and a stationary part of the cleaner.

8. In a vacuum cleaner, a casing member having an opening for discharge of air, a coupling member fitting said opening, a cylindrical container having peripheral perforations, an air vane mounted interiorly thereof adjacent said perforations, one end of said container having perforations, means for seating said container in said opening and within said coupling member, said arrangement permitting application of air through said peripheral perforations and discharge of air through said end perforations.

9. In a vacuum cleaner, a casing having an air outlet port, means in said casing for producing flow of air, a receptacle containing vaporizable insecticide, means for mounting said receptacle so that the receptacle is inside the outlet port and entirely contained within the casing, and means for causing the air within said receptacle to whirl and agitate the material therein.

10. In a vacuum cleaner, a receptacle containing insecticide of the class comprising para-dichlorobenzol and para-dibromobenzol crystals, means for mounting said receptacle so that said receptacle is entirely within said cleaner, an air vane in said receptacle causing the air to whirl in the receptacle and to agitate the insecticide therein, means for passing an air stream therethrough, and means for heating said stream before applying the same to said receptacle whereby the vaporization of said crystals is accelerated.

11. For use with a vacuum cleaner including a casing and means for producing flow of air through said casing, a receptacle for vaporizable material made of cardboard having a substantially cylindrical outside wall, an air inlet in said cylindrical wall, a vane adjacent said air inlet, said vane causing the air to whirl in said receptacle to agitate material therein, said receptacle serving to hold the material before use and means for supporting said receptacle in operative relation to said casing for passage of air through said receptacle.

12. For use with a vacuum cleaner including a casing and means for producing flow of air through said casing, a receptacle for vaporizable material made of cardboard having a substantially cylindrical outside wall, an air inlet in said cylindrical wall, a vane adjacent said air inlet, said vane causing the air to whirl in said receptacle to agitate material therein, said receptacle serving to hold the material before use and means for supporting said receptacle in operative relation to said casing for passage of air through said receptacle, said vane being movable to close said air inlet.

13. For use with a vacuum cleaner including a casing and means for producing flow of air through said casing, a receptacle for vaporizable material made of cardboard and having air inlet and outlet openings and a vane for whirling air therein, a cover for said receptacle to prevent vaporization of material therein before use, and means for supporting said receptacle in operative relation to said casing for passage of air through said receptacle.

LARS ELL.